US008855400B2

(12) United States Patent
Wang et al.

(10) Patent No.: US 8,855,400 B2
(45) Date of Patent: Oct. 7, 2014

(54) DETECTION OF THIN LINES FOR SELECTIVE SENSITIVITY DURING RETICLE INSPECTION USING PROCESSED IMAGES

(75) Inventors: Zhengyu Wang, Santa Clara, CA (US); Rui-fang Shi, Cupertino, CA (US); Lih-Huah Yiin, Mountain View, CA (US); Bing Li, Milpitas, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 321 days.

(21) Appl. No.: 13/473,299

(22) Filed: May 16, 2012

(65) Prior Publication Data

US 2013/0236083 A1     Sep. 12, 2013

Related U.S. Application Data

(60) Provisional application No. 61/608,268, filed on Mar. 8, 2012, provisional application No. 61/609,359, filed on Mar. 11, 2012, provisional application No. 61/609,903, filed on Mar. 12, 2012.

(51) Int. Cl.
*G06K 9/62*     (2006.01)

(52) U.S. Cl.
USPC .......................................................... 382/144

(58) Field of Classification Search
None
See application file for complete search history.

(56) References Cited

U.S. PATENT DOCUMENTS

| 7,873,204 | B2 | 1/2011 | Wihl |
| 8,090,189 | B1 | 1/2012 | Phalke et al. |
| 2010/0251203 | A1 | 9/2010 | Abrams et al. |
| 2011/0299759 | A1* | 12/2011 | Shi et al. ........................ 382/144 |

FOREIGN PATENT DOCUMENTS

SU     884179 A1     11/1981

* cited by examiner

*Primary Examiner* — Brian P Werner
(74) *Attorney, Agent, or Firm* — Kwan & Olynick LLP

(57) ABSTRACT

A detection method for a spot image based thin line detection is disclosed. The method includes a step for generating a band limited spot image from a transmitted and reflected optical image of the mask. The spot image is calibrated to minimize a plurality of optical aberrations from the spot image. The spot image is restored back to a mask image to allow at least one of: a more reliable segmentation between thin line and non-thin line areas on the mask image or a more accurate line width measurement for facilitating segmentation. Thin line features and non-thin lines features are distinguished on the restored mask image. Areas containing thin line features are grown while preventing the thin line growth from encroaching the non-thin line features.

21 Claims, 5 Drawing Sheets

DETECTION OF THIN LINES FOR SELECTIVE SENSITIVITY DURING RETICLE INSPECTION USING PROCESSED IMAGES

CROSS-REFERENCE TO RELATED APPLICATIONS

This application claims the benefit of the following prior applications: (i) U.S. Provisional Application No. 61/608,268, filed Mar. 8, 2012, titled "IMPROVED DETECTION OF THIN LINE FOR SELECTIVE SENSITIVITY DURING RETICLE INSPECTION USING PROCESSED IMAGES" by Zhengyu Wang et al., (ii) U.S. Provisional Application No. 61/609,359, filed Mar. 11, 2012, titled "DETECTION OF THIN LINES FOR SELECTIVE SENSITIVITY DURING RETICLE INSPECTION USING PROCESSED IMAGES" by Zhengyu Wang et al., and (iii) U.S. Provisional Application No. 61/609,903, filed Mar. 12, 2012, titled "DETECTION OF THIN LINES FOR SELECTIVE SENSITIVITY DURING RETICLE INSPECTION USING PROCESSED IMAGES" by Zhengyu Wang et al., which applications are herein incorporated by reference in their entirety for all purposes.

TECHNICAL FIELD OF THE INVENTION

The invention generally relates to a field of reticle inspection. More particularly the present invention relates to a method to detect thin lines using a reticle inspection tool.

BACKGROUND

As densities and complexities of integrated circuits (ICs) continue to increase, inspecting photolithographic mask patterns become progressively more challenging. Every new generation of ICs has denser and more complex patterns that currently reach and exceed optical limitations of lithographic systems. To overcome these optical limitations, various Resolution Enhancement Techniques (RET), such as Optical Proximity Correction (OPC), have been introduced. For example, OPC helps to overcome some diffraction limitations by modifying photomask patterns such that the resulting printed patterns correspond to the original desired patterns. Such modifications can include perturbations to sizes and edges of main IC features, i.e., printable features. Other modifications involve additions of serifs to pattern corners and/or providing nearby sub-resolution assist features (SRAFs), which are not expected to result in printed features and, therefore, are referred to as non-printable features. These non-printable features are expected to cancel pattern perturbations that would otherwise have occurred during the printing process. However, OPC makes mask patterns even more complex and usually very dissimilar to resulting wafer images. Furthermore, OPC defects often do not translate into printable defects.

Non-printable and printable features have different effects on resulting printed patterns and often need to be inspected using different inspection parameters, e.g., sensitivity levels. Areas containing non-printable features are typically "desensed" to avoid fake positives during inspection. Conventional inspection methods generally rely on user defined characteristics, such as feature sizes, for differentiating between printable and non-printable features.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In general, certain embodiments of the invention use processed mask images, instead of the original optical images, for thin line (or non-printable feature) detection. The use of processed mask images results in improved segmentation and main feature protection. Certain embodiments of the invention include: construction of a band limited spot image from transmitted and reflected optical images that are used for thin line detection purpose; an option to calibrate and compensate optical aberrations from the spot image; a way to restore a mask pattern from the spot image, to allow more reliable ID segmentation and more accurate line width measurement; and a way to distinguish thin line and larger geometries and prevent thin line growth from encroaching large geometries.

In one embodiment, a method for inspecting a photolithographic mask to identify lithographically significant defects is provided. A mask comprising a plurality of printable features and a plurality of non-printable features is provided. The mask is configured to achieve lithographic transfer of the printable features onto a substrate using a lithography system. A transmitted image and a reflected image of the mask is produced by one or more inspection systems. A band limited spot image is constructing based on the transmitted and reflected images to reduce noise introduced by the inspection apparatus. The spot image is restored to a mask image to thereby minimize further optical aberrations from the one or more inspection systems in the mask image. The restored mask image is used to generate a non-printable feature map for the non-printable features and printable feature map for the printable features. The non-printable feature map is expanded (or grown) while preventing encroachment of such non-printable feature map into the printable features based on the printable feature map. One or more test images of the mask may then be analyzed to detect defects on such mask, wherein a sensitivity level of defect detection is reduced in areas of the one or more test images defined by the non-printable feature map, as compared with areas of the one or more test images that are not defined by the non-printable features map.

In specific implementations, a thinning process is performed on the restored mask image to generate a skeleton image, and line widths are measured in the restored mask image using the skeleton image to determine where to measure such line widths. The measured line widths are used to generate the non-printable and printable feature maps by distinguishing between measured line widths that are below or equal to or above a specified threshold value, respectively. In another embodiment, generation of the band limited spot image is accomplished by combining the reflected and transmitted images into a linear equation with selected coefficients so that high frequency terms cancel each other out. In a further aspect, the spot image is processed using calibration data to remove further optical aberrations from the spot image. In another aspect, each feature that has a measured line width below the predefined threshold value is only included in the non-printable map if such feature is within a predefined distance to another feature that has a measured line width equal to or above the predefined threshold value. In yet another embodiment, restoring the spot image to the mask image results in the mask image being deblurred and a truer image of the mask.

In certain embodiments, the invention pertains to a system for inspecting a photomask to identify lithographically significant defects that includes at least one memory and at least one processor that are configured to perform at least some of the above described operations. In other embodiments, the invention pertains to computer readable media having instructions stored thereon for performing at least some of the above described operations.

In another embodiment, detection method for thin line detection on a mask is disclosed. The method comprises (i) generating a band limited spot image from a transmitted and reflected optical image of the mask; (ii) calibrating the spot image to minimize a plurality of optical aberrations from the spot image; (iii) restoring the spot image back to a mask image to allow at least one of: a more reliable segmentation between thin line and non-thin line areas on the mask image or a more accurate line width measurement for facilitating segmentation; (iv) distinguishing between thin line features and non-thin lines features on the restored mask image; and (v) growing areas containing thin line features while preventing the thin line growth from encroaching the non-thin line features.

In a specific embodiment, preventing the thin line growth from encroaching the plurality of geometries is accomplished by distinguishing the thin line and non-thin features. In another aspect, the detection method further includes a step of utilizing level-set function to measure critical dimensions for performing thin line detection. In another features, the step of restoring the mask pattern from the spot image allows more reliable segmentation and more accurate line width measurement. In yet another embodiment, the spot image is a band limited low passed version of the mask pattern.

These and other aspects of the invention are described further below with reference to the figures.

DETAILED DESCRIPTION OF EXAMPLE EMBODIMENTS

Figure 1A:
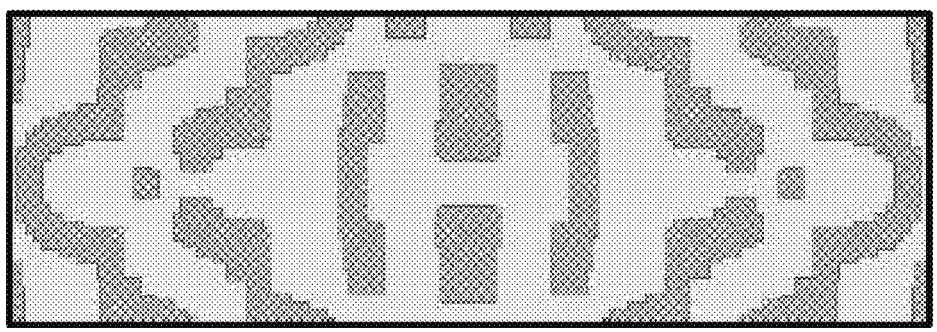
FIG. 1A illustrates a base pattern provided on a photomask in accordance with certain embodiments.

In the following description, numerous specific details are set forth in order to provide a thorough understanding of the present invention. The present invention may be practiced without some or all of these specific details, in other instances, well known process operations have not been described in detail to not unnecessarily obscure the present invention. While the invention will be described in conjunction with the specific embodiments, it will be understood that it is not intended to limit the invention to the embodiments.

Introduction

One photomask inspection method uses an approach for separating printable features (also referred to as main features) from non-printable ones (also referred to as thin lines) for later "de-sensing" areas containing non-printable features. A test image and/or reference image are used to create a feature map based on a rule set by a user. Usually, a user defines a line width as criteria for separating non-printable features from printable ones.

One approach may start with capturing reference and test images. An example technique is described in U.S. Pat. No. 8,090,189 to Vinayak Phalke et al., which is incorporated herein by reference in its entirety for all purposes. In general, an intensity threshold is applied to these images to define a foreground of the features, which is a collection of the image areas with intensity values below this threshold.

Photomasks are often designed with different types of thin lines, such as opaque thin lines and clear thin lines, which add additional complexities in defining a foreground. Opaque thin lines are thin stripes or dots of molybdenum-silicon that appear darker than their surroundings on a transmitted image. On the hand, clear thin lines are thin stripes or dots of cuts made on molybdenum-silicon/chrome surfaces that appear darker than these surrounding surfaces on a reflected image. Furthermore, in a die-to-die inspection, defect areas are not apparent from the test and reference images. As such, a combined analysis of the reference and test images needs to be performed. In a next operation, line widths of foreground features are measured to differentiate between thin lines and main features to form a "raw" feature map. A rule for this line width threshold is typically set by a user.

When generating an optical image, distortions in the image may result in overshoot or undershoot of particular features, e.g., due to blurring or other optical distortions. For example, OMOG (Opaque MoSi on Glass) reflected images may result in high undershoot. Such effects often tend to complicate the segmentation process. For example, overshoots may serve as distractions in the segmentation process and have to be analyzed more carefully to determine how to segment the particular overshoot feature into a thin line or non-thin line. In sum, overshoots and undershoots can add complexity to the segmentation process.

The line width definition tends to be subjective and depends on a single threshold (contour level) which is arbitrarily chosen by a user. The line width as a result has no direct correlation with the underlying mask pattern's true dimension. It often results in the user having to reiterate multiple times to find the threshold to properly segment thin lines. Additionally, a user often needs to set the contour level for both the clear thin line and the opaque thin line separately which doubles the amount of setup work. Finally, when a thin line's line width is small, or when a thin line has other patterns in its close neighborhood, the modulation of the thin lines can vary a lot. Sometimes it is simply impossible to find a single contour level to segment all thin lines of the same tone.

Additionally, this prior approach does not specify large geometry protection due to the nature of thin line detection. For example, a defective main feature (printable feature) can appear in the neighborhood of a detected thin line, and a dilation margin is usually applied to expand the original detected thin line to cover some neighborhood area, which may then encompass the defective main feature. Without main feature protection, such dilation has the risk of running into main features, as well as associated defects, and as a result de-sense lithographically critical defects on large printable geometries in the neighborhood of a non-printable thin line.

Figure 1B:
FIG. 1B illustrates a resulting wafer image of the base pattern in FIG. 1A after a lithographic transfer.
Figure 1B:
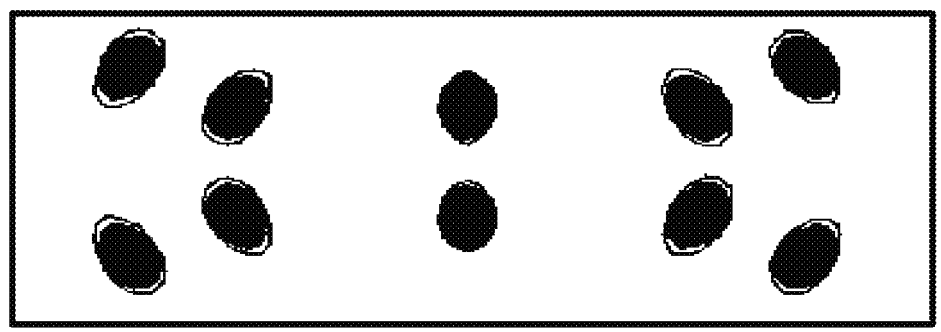

Some of the above issues can be further illustrated in the following example. FIG. 1A illustrates an illustrative base pattern provided on a photomask, while FIG. 1B illustrates a resulting wafer image of that base pattern. There is very little, if any, resemblance between the two images. Extensive uses of OPC lead to such discrepancies.

Inspecting Methods Examples

Figure 2:
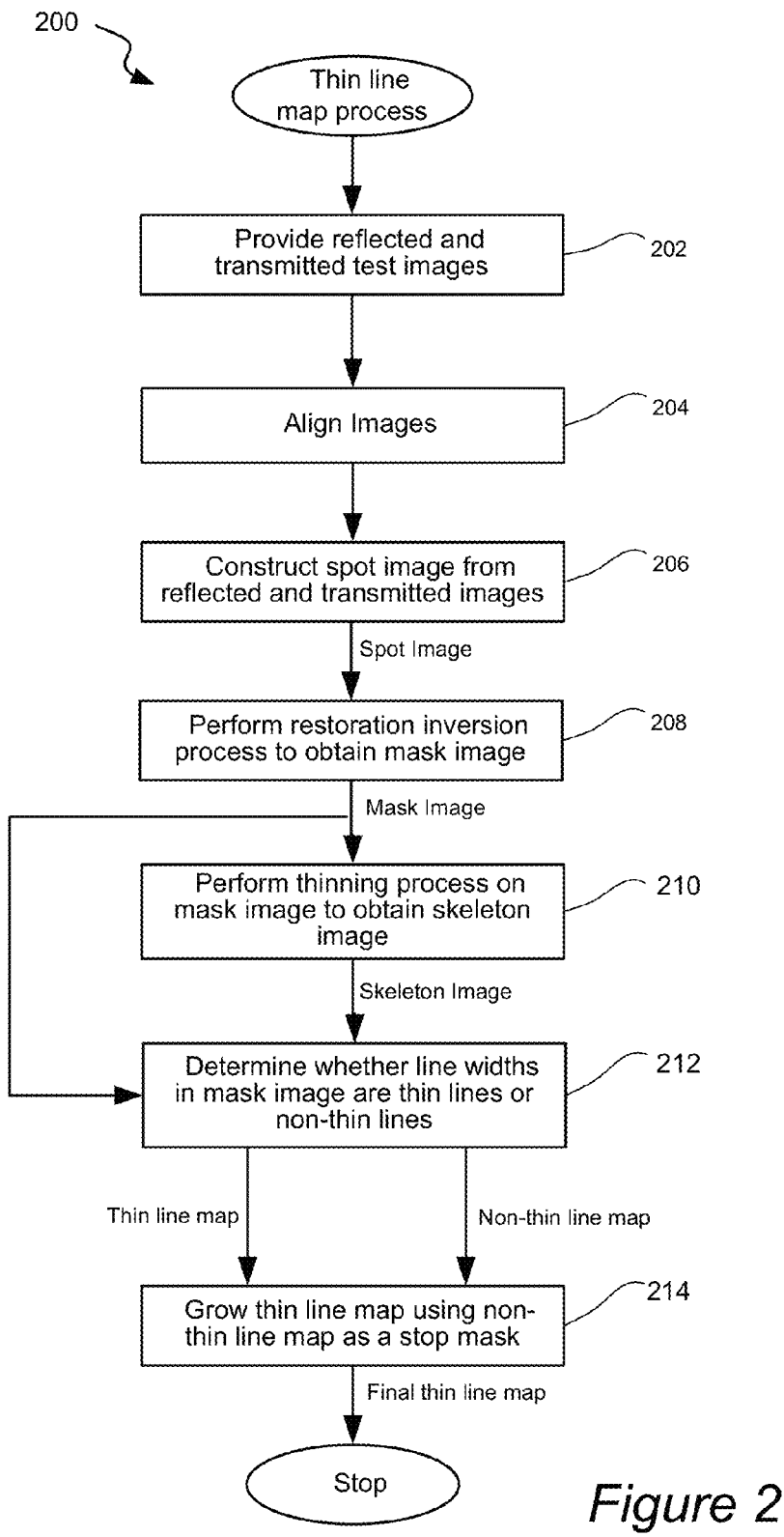
FIG. 2 is a flowchart of a procedure for thin line detection for a photomask based on a band limited spot image according to an exemplary embodiment of the present invention.

FIG. 2 is a flowchart of a procedure 200 for thin line detection for a photomask based on a band limited spot image according to an exemplary embodiment of the present invention. In the examples described herein, thin line detection includes detection of any non-printable of lithographically insignificant feature of the photomask. The terms "thin line", "non-printable", and "lithographically insignificant" are used herein interchangeably.

In general, any suitable type of photomask (reticle) may be used in the process. For example, a photomask made from a transparent fused silica blank with a pattern defined by a chrome metal adsorbing film can be used. In general, a photomasks or mask may take the form of any suitable type of reticle or photomask, e.g., phase shift masks, and Embedded Phase Shift Masks (EPSMs). A photomask generally includes a plurality of printable features and a plurality of non-printable features.

A printable feature can be defined as a feature that appears on a resulting wafer image. Such printed feature may or may not be present on the resulting wafer in the same shape or form as on a photomask. For example, FIG. 1A illustrates a base pattern provided on a photomask, while FIG. 1B illustrates a resulting wafer image of that base pattern. Therefore, in the context of a photomask, a printable feature may be understood as an area corresponding to the printable feature on a wafer plane. Non-printable features (or "thin lines") may include various optical proximity correction (OPC) features that are used to compensate for imaging errors due to diffraction and other reasons. One type of such non-printable features is sub-resolution assist features (SRAF).

Once the photomask is provided for the inspection process, e.g., placed on an inspection stage of the inspection system, a reflected image and a transmitted image of the photomask are provided in operation 202. More generally, the photomask may be illuminated to capture two or more light intensity images at different illumination and/or collection conditions. In illustrated embodiment, a transmitted light intensity image and a reflected light intensity image are captured. In other embodiments, two or more other types of images may be used.

The captured test images are typically aligned in operation 204. This alignment may involve matching optical properties of the inspection system(s) for multiple test and reference images. For example, in the case of transmitted and reflected images, some adjustment of the images can be made to compensate for differences in optical paths of the two respective signals. Alignment adjustments may depend on specific geometries of an inspection system used. In the illustrated embodiment, alignment involves aligning the transmitted image with respect to the reflected image.

Once aligned, a spot image may be constructed based on the reflected and transmitted images in operation 206. The spot image is also referred to as a band limited mask image. The process for constructing a spot image may generally include substantially eliminating optical noise from the transmitted and reflected images to obtain a resulting spot image. In general, high frequency effects are substantially reduced or eliminated. For example, rings that are formed around particular reticle patterns due to optical effects of the inspection system are removed in the spot image. The spot image results in a reduction in the amount of overshoot and undershoot, which could otherwise distract thin lines detection. That is, noise in the mask image is substantially reduced, and such noise can no longer be detected as thin lines. The reflected and transmitted images can be combined with selected coefficients in a linear combination so that the high frequencies terms cancel each other out. As a result, the spot image is a band limited low passed version of the mask pattern image.

In one approach, partially coherent optical imaging can be modeled as a sum of two or more coherent systems, which is further explained in more detail in U.S. Pat. No. 7,873,204 by Wihl et al, which is incorporated herein by reference for purposes of describing operation 206. In this example implementation, the Hopkins equations for partially coherent imaging can be used to form a Transmission-Cross-Coefficient (TCC) matrix. This matrix can be then decomposed into corresponding Eigen vectors, which act as kernels of coherent systems. The Eigen value weighted sum of the intensity contributions from each of these coherent systems yields the image intensity, which can be used to represent the intensity of the transmitted signal. In certain embodiments, reflected and transmitted intensities of the test images can be represented with only linear terms that are referred to as band limited mask amplitude functions. An example of this function is presented in Equation 1.

$$\frac{\|a_R\|^2(I_T(x,y) - \|c_T\|^2) - \|a_T\|^2(I_R(x,y) - \|c_R\|^2)}{2\|a_R\|^2 \mathrm{Re}(a_T \overset{*}{C_T}) - 2\|a_T\|^2 \mathrm{Re}(a_R c_R^*)} = $$

$$\sum \lambda_i D_i [P(x,y) \oplus E_i(x,y)] =$$

$$P(x,y) \oplus \sum_{i=0}^{N} \lambda_i D_i E_i(x,y) = M(x,y)$$

[Equation 1]

where $a_R$ is the complex reflected amplitude of the difference between the mask foreground tone and the background tone; $I_T(x,y)$ describes the transmitted intensity image of a mask using the inspection system; $C_T$ is the complex transmitted amplitude of the background tone of the mask (e.g., in a quartz and chrome binary mask $C_T$ can describe properties of the chromium pattern); $a_T$ is the complex transmitted amplitude of the difference between the mask foreground tone and the background tone (e.g., using the same mask as above $a_T$ can describe the optical properties of the difference between the quartz and the chromium; $c_T$ and $a_T$ of course vary depending on the properties of the material layers described); $I_R(x,y)$ describes the reflected intensity image of a mask using the inspection system; $C_R$ is the complex reflected amplitude of the background tone of the mask and $a_R$ is the complex reflected amplitude of the difference between the mask foreground tone and the background tone; Re(x) represents the real component of x; P(x,y) defines the mask pattern of the photomask being inspected; $E_i$ and $\lambda_i$ refer, respectively, to the Eigen Vectors and Eigen Values of associated elements of a transmission cross-coefficient (TCC) imaging matrix associated with the inspection tool; $D_i$ is the DC gain of $E_i$.

The band limited mask pattern M(x,y) is defined by the mask pattern P(x,y) convolved with a function:

$$\frac{\|a_R\|^2(I_T(x,y) - \|c_T\|^2) - \|a_T\|^2(I_R(x,y) - \|c_R\|^2)}{2\|a_R\|^2 \text{Re}(a_T \overset{*}{C}_T) - 2\|a_T\|^2 \text{Re}(a_R c_R^*)} =$$ [Equation 1]

$$\sum \lambda_i D_i[P(x,y) \oplus E_i(x,y)]$$

$$= P(x,y) \oplus \sum_{i=0}^{N} \lambda_i D_i E_i(x,y) = M(x,y)$$

which is referred to as a "recovery kernel". Therefore, the band limited mask pattern is a modified version of the mask pattern function P(x,y).

Although combining the reflected and transmitted images results in some high frequency portions of the image, which are due to optical effects, to be cancelled, the spot image construction is still an approximation of the "true" mask (e.g., without aberrations) because some aberrations remain in the spot image. In a further embodiment, the constructed spot image can be processed to compensate for certain aberrations. For example, a method can be used to calibrate static aberrations offline and then filter aberration effects from the spot image. In general, a variety of patterns may be fabricated on a calibration mask and then imaged. The aberration terms in the calibration image can then be extracted for the different patterns. The extracted aberration terms can then be subtracted from images of similar patterns of the spot image so that such aberration terms are removed from the spot image.

After the spot image is constructed, a restoration inversion process may be performed to obtain a restored mask image in operation 208. That is, a more "true" or binary-like mask image is derived from the spot image in an inversion process. For example, patterns in the spot image that may be blurred by the optics are sharpened to form a mask image. For very thin line or thin line that is not well separated from other patterns in the neighborhood, this post-processing will facilitate easier and less ambiguous segmentation.

For a die-to-die inspection process, a simple high pass with automatic threshold may be used so as to create sharper transitions in the spot image. In certain inspection tools, such as the StarLight™ available from KLA-Tencor Corp. of Milpitas, Calif., a level-set based inversion is provided in the tool to deduce the underlying mask pattern. An example level set function is described in U.S. Pat. Application Pub. No. 2010/0251203 by Daniel Abrams, filed 30 Sep. 2010, which application is incorporated herein by reference for describing a level-set process. A level set function can be used to define the boundaries (or contours) on the mask, which function is incrementally and iteratively adjusted until the restored mask image is found. For each set of mask contours, the optical inspection tool, which was used to obtain the original mask image, is modeled or simulated on the set of mask contours to result in a simulated spot image. The mask contour set is adjusted and a simulated spot image based on each adjusted set of contours is generated until a simulated spot image most closely matches the constructed spot image. For example, a minimum difference is achieved. The set of mask contours that results in a simulated spot image that most closely matches the constructed spot image can then be defined as the restored mask image.

The level set function may take any suitable form for defining the boundary of each image mask feature. In one embodiment, the level set function is equal to 0 at the boundary or contour; less than 0 for outside the contour; and more than 0 for inside the contour. The level set 0 function (or whatever function defines the contours) can be used to measure critical dimension (CD) on the mask image. That is, CD can be directly measured on the $0^{th}$ level set function (or the defined contours). For example, four CD measurements on each feature contour may be taken in four directions and the minimum is defined as the CD for such feature.

Figure 3:
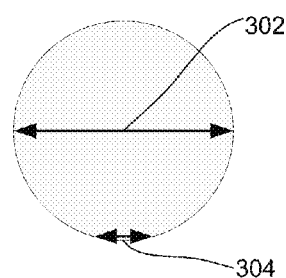
FIG. 3 illustrates obtaining varying line widths at different locations on a circle contour.

The resulting mask image includes patterns, geometries, features, shapes, etc. ("patterns"), and the patterns are typically defined by a set of contours, lines, boundaries, edges, curves, etc. ("contours"), which generally surround, enclose, and/or define the boundary of the various regions which constitute a pattern on the mask. Line width may be difficult to ascertain on particular contours. For example, the line width measurement of a circle contour may vary depending on where the measurement is obtained as illustrated in FIG. 3. As shown, a line width 302 measured through the center of the circle will be much larger than a line width 304 measured through an edge of the circle.

Accordingly, a process may be used to determine where to measure line widths on the image mask. In one embodiment, a thinning process may be performed on the mask image to obtain a skeleton image in operation 210. In general, each pattern of the mask image is reduced in size so as to provide a site or location in the mask image for later measuring line width on the particular mask image pattern. For instance, the skeleton for a circle is a pixel in the center of the circle so that the line width is obtained through the center of the circle on the mask image, and the skeleton for a line is a line that is 1 pixel wide so that the line width of the line can be obtained anywhere along the line's longitudinal axis.

After the mask image is thinned to produce a skeleton image, the skeleton and mask images are then used to determine whether line widths in the mask image can be defined as thin line patterns or non-thin lime patters in operation 212. This line width check results in both a thin line map and a non-thin line map. In general, the skeleton image is used to measure line widths on the mask image and compare the measured line widths to a line width specification for thin lines (or non-thin lines). If the measured line width is less than the line width specification, the associated pattern is defined as a thin line. The line width check may also include only defining a feature as a thin-line if such feature is within a predefined proximity to a non-thin feature. If the measured line width is equal to or greater than the line width specification, the associated pattern is defined as a non-thin line. Thus, particular patterns on the mask image can be defined as thin line or non-thin line areas to produce both a thin line and non-thin line map.

For die-to-die, the binary mask image can first be normalized and then a template pixel algorithm can be applied. In general, this process may include comparing the rate of change of pixel intensity in the neighborhood of a test pixel, which is defined by the skeleton image, against the theoretical drop off for a thin line (e.g., SRAF) of a given size or line width.

When a level set function is provided, the zero crossing of the function is the particular contour itself. A direct measurement of line width on this contour along multiple directions can be performed. Finally, taking the minimum of these measurements can then be used to approximate the line width. For main feature protection, the line width check can be the sole criteria to decide if a pattern is thin line or large line pattern.

Further when pixels have the same tone as the thin line, but their line widths are larger than the user defined line width specification, such pixels can be treated as non-thin line pixels. These non-thin line pixels form the large geometry map (or non-thin line map) image that needs to be protected against thin line growth. During thin line growth, this image can be used as the mask to stop unwanted growth in operation 214. Thus, thin line growth is prevented from encroaching large geometries areas of the mask image to result in a final thin-line map (or inversely non-thin line map), referred to herein as a feature map.

Figure 4:
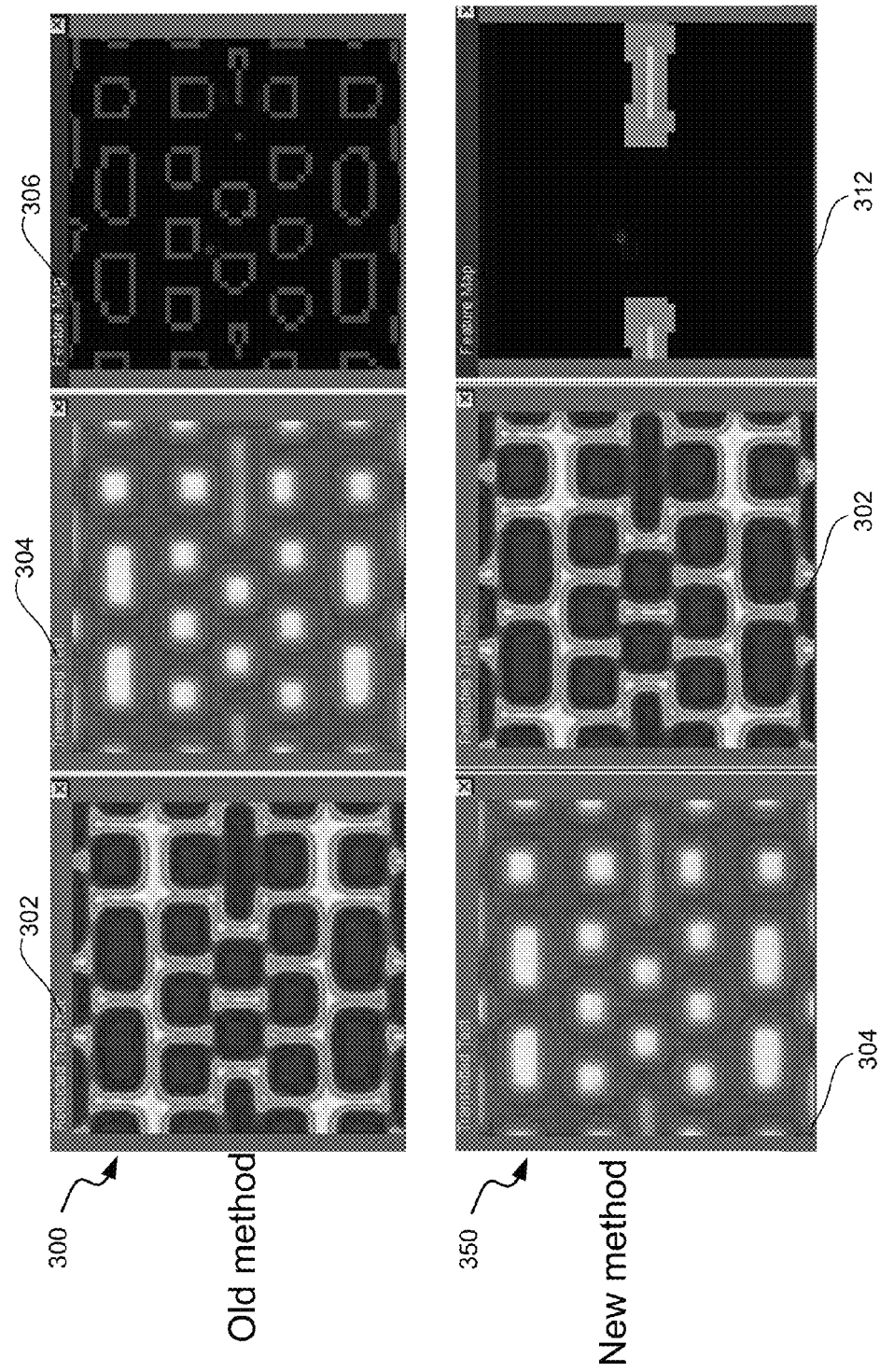
FIG. 4 is a screenshot of an inspection report according to an exemplary embodiment of the present invention.

FIG. 4 is a screenshot of an inspection report according to an exemplary embodiment of the present invention compared to an older process. The reflected optical image 302 shows a large amount of undershoot. The thin line map is shown as "feature map" (306 for old method and 312 for the spot-image method). A dark background in each feature map (306 and 312) indicts that there is no thin line found. The dark gray lines in the "feature map" 306 from the old method are thin line candidate pixels, but were rejected later or other reasons. They are only shown for illustration purposes. The bright white lines in the "feature map" 312 from the new method are thin line pixels that passed further checks including line width check and closeness to main features, and therefore are accepted as true thin lines. The light gray areas surrounding the white lines are thin line growth to cover the neighborhood to a user specified extent.

As can be seen in FIG. 4, the old method failed to segment the two thin lines due to them closely butting against other patterns. Instead the old method was distracted by some candidate thin line pixels on the edge of contacts due to undershoot despite such pixels being disqualified later for other reasons. The new method instead, not only caught the thin lines properly, but avoided distraction from the false thin line candidates. The resulting feature map is not only more accurate, but also more robust and computationally more efficient with less distraction.

The different approaches used in die-to-die and selection of a set level function option are considered alternative aspects. Advantages of certain embodiments of the present invention may include more reliable thin line segmentation because it largely avoids overshoot or undershoot present in the optical images. Certain embodiments may also largely overcomes the limitation of die-to-die thin line detection where it may be very difficult or impossible to segment thin lines of different modulation and those close to neighbor patterns. Certain embodiments may also be more user friendly because it automatically selects contour, instead of making user arbitrarily set contour. Further, a single contour can be used for both clear and dark thin line, instead of two contours. Thin line measurement may also be better correlated with underlying thin line width on the mask, and thin line growth into de-sense critical defects on large geometries may be avoided.

Figure 5:
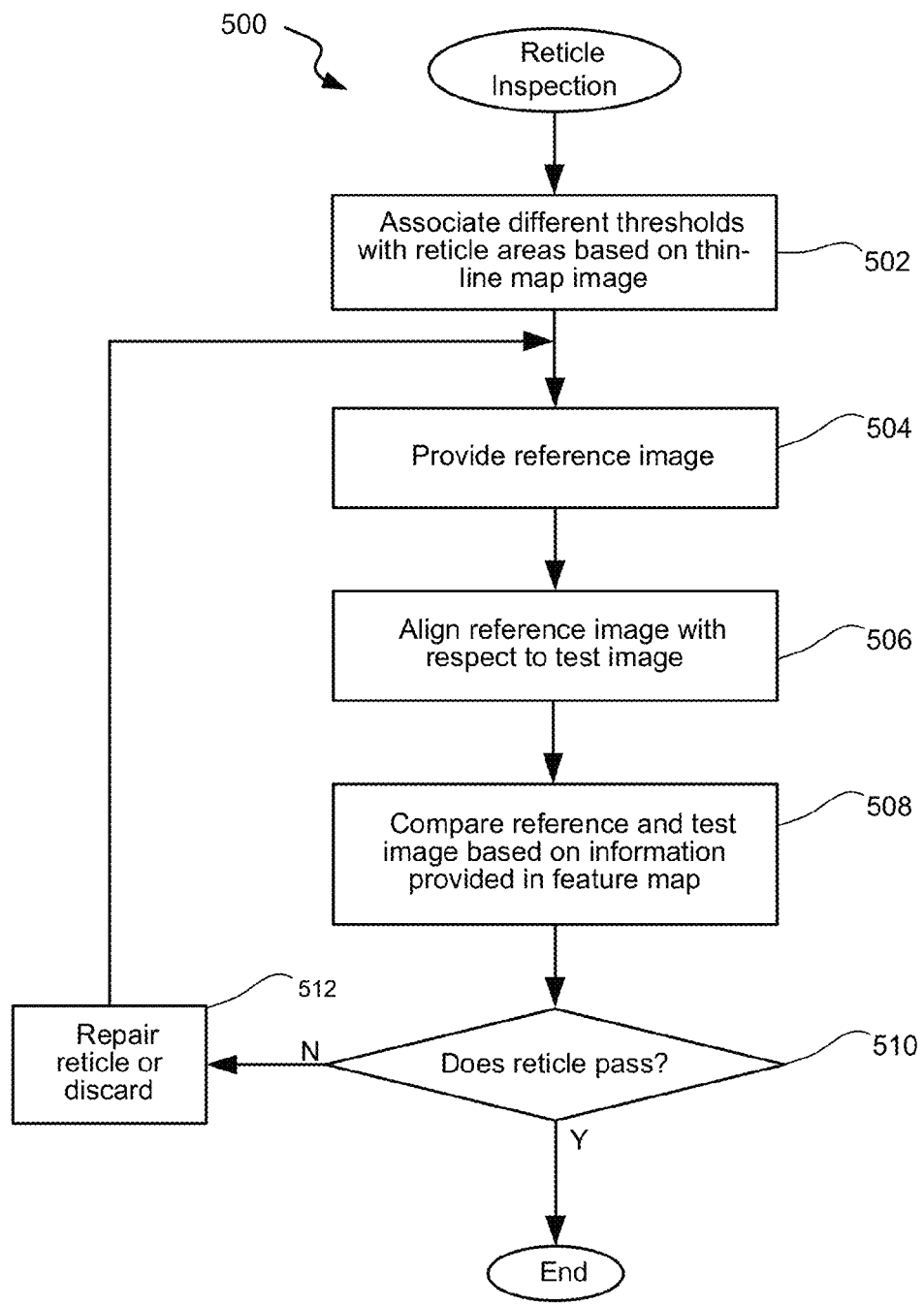
FIG. 5 is a flowchart illustrating a reticle inspection procedure in accordance with one embodiment of the present invention.

FIG. 5 is a flowchart illustrating a reticle inspection procedure 500 in accordance with one embodiment of the present invention. Initially, different inspection thresholds may be associated with different reticle areas based on the final feature map in operation 502. Photomask inspection methods may involve providing one or more user-defined detection thresholds. For example, areas defined as main features by the feature map may be assigned one detection threshold, while areas containing SRAFs or other non-printable thin line feature may be assigned a lower threshold. This differentiation can be used to optimize inspection resources.

A reference image may be provided in operation 504. For example, another image of a die area on the reticle is obtained for a die-to-die type inspection. In a die-to-database inspection, a reference image is generated based on the design database. For example, the inspection optics are modeled and applied to the design patterns to obtain a reference image. The reference image may be aligned with respect to the test image in operation 506. Both the test and reference images may be mask recovered spot images as described herein or "raw" images obtained from the inspection tool.

In operation 508, the reference image is compared to test image based on information contained in the feature map. For example, test and reference images may be divided into multiple areas identified in the feature map. Each set of areas containing a test image area and a corresponding reference image area may be inspected individually, MEEFs, user defined thresholds, geometrical map, and other information specific for each area may be used in this operation. In other words, analysis of the test image may involve identifying portions of the test image and corresponding portions of the reference image and identifying any differences in these images for each identified portion. In a specific embodiment, differences are identified between aligned test transmitted and reference transmitted images and between aligned test reflected and the reference reflected images.

It may then be determined based on the comparison results whether the reticle passes inspection in operation 510. If the reticle passes, the inspection process may end, and fabrication may proceed using the passing reticle. If the reticle does not pass, the reticle can either be repaired or discarded in operation 512 and inspection ends.

In general, the feature map can be specifically used to define and focus on areas that contain lithographically significant features and defects during reticle inspection. The map can be used to provide instructions to the inspection system to "de-sense" areas defined as thin-line or nonprintable features during inspection. For example, areas containing only thin lines (e.g., SRAFs) may be inspected with lower sensitivity, than areas containing main features (printable or non-thin line features). As indicated above, areas of the thin line feature map distinguish between these two types of features. Overall, novel processes and inspection systems described herein allow a more effective reticle inspection process.

In yet another embodiment, the method may also include constructing a geometrical map based on the band limited mask pattern for classifying geometrical features into one or more geometrical feature types, such as edges, corners, and line ends. Furthermore, a process of identifying the lithographically significant defects can be enhanced by applying different detection thresholds to different geometrical feature types of the geometrical map.

In certain embodiments, inspection is applied to multiple tone masks as well. One example of such masks are tri-tone masks having a darkest region (e.g., a chrome or opaque regions) and a quartz or lightest region with a pattern of grey scale regions having a darkness between the two. Such grey scale regions can be obtained in a number of ways (e.g., using EPSM materials and so on). In this case, the mask is treated as two different masks that are separately analyzed. For example, a tri-tone mask can be treated using the same techniques as described above. However, the tri-tone mask can be treated as a mask having a background pattern (e.g., chromium) with the grey scale pattern (e.g., EPSM material) treated as the foreground. The images can be processed as above using the same equations and process operations. A second analysis is performed on the mask using the EPSM material as the background pattern and the lightest pattern (e.g., the quartz) treated as the foreground. Alignment can easily be effectuated because each of the materials have substantially differing properties that demonstrate different edge effects which can be used to align the images. The mask patterns can then be summed and then compared to references in die-to-die or die-to-database comparisons to verify wafer pattern correctness throughout the process window and to identify lithographically significant defects.

System Examples

Figure 6A:
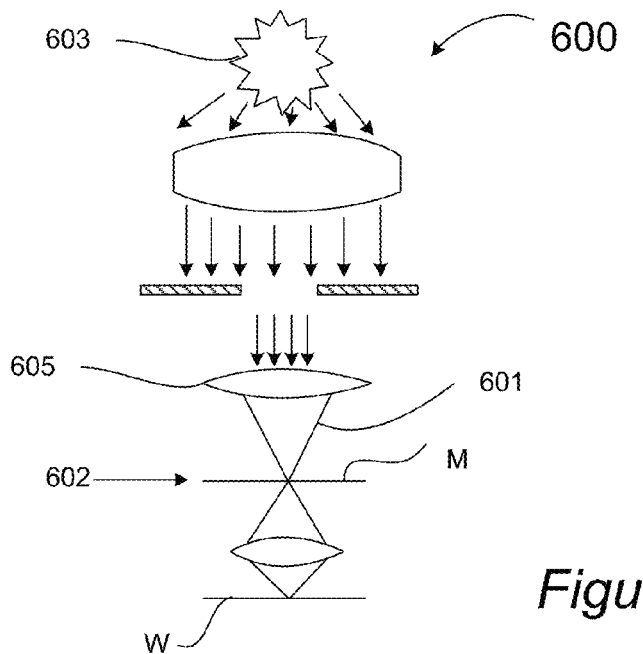
FIG. 6A is a simplified schematic representation of a lithographic system for transferring a mask pattern from a photomask onto a wafer in accordance with certain embodiments.

FIG. 6A is a simplified schematic representation of a typical lithographic system 600 that can be used to transfer a mask pattern from a photomask M onto a wafer W in accordance with certain embodiments. Examples of such systems include scanners and steppers, more specifically PAS 5500 system available from ASML in Veldhoven, Netherlands. In general, an illumination source 603 directs a light beam through an illumination lens 605 onto a photomask M located in a mask plane 602. The illumination lens 605 has a numeric aperture 601 at that plane 602. The value of the numerical aperture 601 impacts which defects on the photomask are lithographic significant defects and which ones are not. A portion of the beam that passes through the photomask M forms a patterned optical signal that is directed through imaging optics 653 and onto a wafer W to initiate the pattern transfer.

Figure 6B:
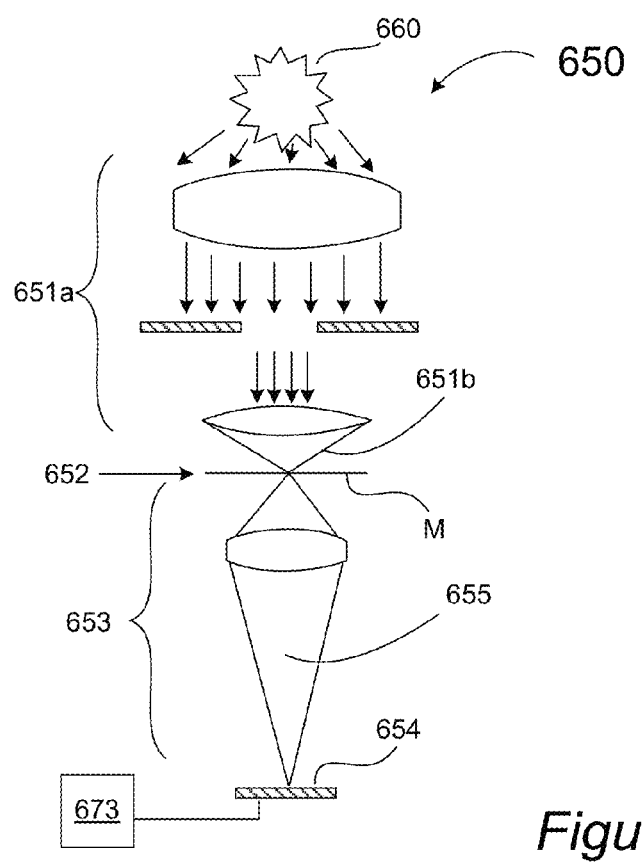
FIG. 6B provides a schematic representation of a photomask inspection apparatus in accordance with certain embodiments.

FIG. 6B provides a schematic representation of an inspection system 650 that has an imaging lens 651a with a relative large numerical aperture 651b at a reticle plane 652 in accordance with certain embodiments. The depicted inspection system 650 includes microscopic magnification optics 653 designed to provide, for example, 60-200× magnification for enhanced inspection. The numerical aperture 651b at the reticle plane 652 of the inspection system is often considerable greater than the numerical aperture 601 at the reticle plane 602 of the lithography system 600, which would result in differences between test inspection images and actual printed images. Each of these optical systems (600, 650) induces different optical effects in the produced images, which are accounted and compensated for in novel inspection techniques described herein.

The inspection techniques described herein may be implemented on various specially configured inspection systems, such as the one schematically illustrated in FIG. 6B. The system 650 includes an illumination source 660 producing a light beam that is directed through illumination optics 651 onto a photomask M in the reticle plane 652. Examples of light sources include lasers or filtered lamps. In one example, the source is a 193 nm laser. As explained above, the inspection system 650 has a numerical aperture 651b at the reticle plane 652 that may be greater than a reticle plane numerical aperture (e.g., element 601 in FIG. 6A) of the corresponding lithography system. The photomask M to be inspected is placed at the reticle plane 652 and exposed to the source.

The patterned image from the mask M is directed through a collection of magnification optical elements 653, which project the patterned image onto a sensor 654. Suitable sensors include charged coupled devices (CCD), CCD arrays, time delay integration (TDI) sensors, TDI sensor arrays, photomultiplier tubes (PMT), and other sensors. In a reflecting system, optical elements would direction and capture the reflected image.

The signals captured by the sensor 654 can be processed by a computer system 673 or, more generally, by a signal processing device, which may include an analog-to-digital converter configured to convert analog signals from the sensor 654 into digital signals for processing. The computer system 673 may be configured to analyze intensity, phase, and/or other characteristics of the sensed light beam. The computer system 673 may be configured (e.g., with programming instructions) to provide a user interface (e.g., on a computer screen) for displaying resultant test images and other inspection characteristics. The computer system 673 may also include one or more input devices (e.g., a keyboard, mouse, joystick) for providing user input, such as changing detection threshold. In certain embodiments, the computer system 673 is configured to carry out inspection techniques detailed below. The computer system 673 typically has one or more processors coupled to input/output ports, and one or more memories via appropriate buses or other communication mechanisms.

Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

In certain embodiments, a system for inspecting a photomask includes at least one memory and at least one processor that are configured to perform the following operations: producing test light intensity images of a mask that include a test transmitted image and a test reflected image, constructing a spot image, restoring the spot image to a mask image, line thinning, creating a feature map, and analyzing the test light intensity images using the feature map to identify photomask defects. One example of an inspection system includes a specially configured TeraScan™ DUV inspection system available from KLA-Tencor of Milpitas, Calif.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. Accordingly, the present embodiments are to be considered as illustrative and not restrictive, and the invention is not to be limited to the details given herein.

What is claimed is:

1. A method for inspecting a photolithographic mask to identify lithographically significant defects, the method comprising:

providing a mask comprising a plurality of printable features and a plurality of non-printable features, the mask configured to achieve lithographic transfer of the printable features onto a substrate using a lithography system;

by one or more inspection systems, producing a transmitted image and a reflected image of the mask;

constructing a band limited spot image based on the transmitted and reflected images to reduce noise introduced by the one or more inspection systems;

restoring the spot image to a mask image to thereby minimize further optical aberrations from the one or more inspection systems in the mask image;

using the restored mask image, generating anon-printable feature map for the non-printable features and printable feature map for the printable features;

growing the non-printable feature map while preventing encroachment of such non-printable feature map into the printable features based on the printable feature map; and analyzing one or more test images of the mask to detect defects on such mask, wherein a sensitivity level of defect detection is reduced in areas of the one or more test images defined by the non-printable feature map, as compared with areas of the one or more test images that are not defined by the non-printable features map.

2. The method of claim 1, further comprising:
performing a thinning process on the restored mask image to generate a skeleton image; and
measuring line widths in the restored mask image using the skeleton image to determine where to measure such line widths,
wherein the measured line widths are used to generate the non-printable and printable feature maps by distinguishing between measured line widths that are below or equal to or above a specified threshold value, respectively.

3. The method of claim 1, wherein generating the band limited spot image is accomplished by combining the reflected and transmitted images into a linear equation with selected coefficients so that high frequency terms cancel each other out.

4. The method of claim 2, further comprising:
processing the spot image using calibration data to remove further optical aberrations from the spot image.

5. The method of claim 2, wherein each feature that has a measured line width below the predefined threshold value is only included in the non-printable map if such feature is within a predefined distance to another feature that has a measured line width equal or above the predefined threshold value.

6. The method of claim 1, wherein restoring the spot image to the mask image results in the mask image being deblurred and a truer image of the mask.

7. The method of claim 1, wherein the analysis of the one or more test images is accomplished by comparing the one or more test images to a reference image obtained from a design database for fabricating the mask.

8. The method of claim 1, wherein the analysis of the one or more test images is accomplished by comparing the one or more test images to a reference image obtained from from a reference die.

9. The method of claim 1, wherein the non-printable features comprise Sub-Resolution Assist Features (SRAF).

10. The method of claim 1, further comprising constructing a geometrical map based on the spot image and for classifying geometrical features into one or more geometrical feature types selected from the group consisting of edges, corners, and line ends, wherein the analysis of the one or more test images is further based on the geometrical map.

11. An inspection system for inspecting a mask to identify lithographically significant defects comprising at least one memory and at least one processor that are configured to perform the following operations:
providing a mask comprising a plurality of printable features and a plurality of non-printable features, the mask configured to achieve lithographic transfer of the printable features onto a substrate using a lithography system;
producing a transmitted image and a reflected image of the mask;
constructing a band limited spot image based on the transmitted and reflected images to reduce noise introduced by the inspection system;
restoring the spot image to a mask image to thereby minimize further optical aberrations from the one or more inspection systems in the mask image;
using the restored mask image, generating a non-printable feature map for the non-printable features and printable feature map for the printable features;
growing the non-printable feature map while preventing encroachment of such non-printable feature map into the printable features based on the printable feature map; and
analyzing one or more test images of the mask to detect defects on such mask, wherein a sensitivity level of defect detection is reduced in areas of the one or more test images defined by the non-printable feature map, as compared with areas of the one or more test images that are not defined by the non-printable features map.

12. The system of claim 11, further comprising:
performing a thinning process on the restored mask image to generate a skeleton image; and
measuring line widths in the restored mask image using the skeleton image to determine where to measure such line widths,
wherein the measured line widths are used to generate the non-printable and printable feature maps by distinguishing between measured line widths that are below or equal to or above a specified threshold value, respectively.

13. The system of claim 11, wherein generating the band limited spot image is accomplished by combining the reflected and transmitted images into a linear equation with selected coefficients so that high frequency terms cancel each other out.

14. The system of claim 12, further comprising:
processing the spot image using calibration data to remove further optical aberrations from the spot image.

15. The system of claim 12, wherein each feature that has a measured line width below the predefined threshold value is only included in the non-printable map if such feature is within a predefined distance to another feature that has a measured line width equal or above the predefined threshold value.

16. The system of claim 11, wherein restoring the spot image to the mask image results in the mask image being deblurred and a truer image of the mask.

17. A detection method for thin line detection on a mask, detection method comprising:
generating a band limited spot image from a transmitted and reflected optical image of the mask;
calibrating the spot image to minimize a plurality of optical aberrations from the spot image;
restoring the spot image back to a mask image to allow at least one of:
a more reliable segmentation between thin line and non-thin line areas on the mask image; and
a more accurate line width measurement for facilitating segmentation;
distinguishing between thin line features and non-thin lines features on the restored mask image; and
growing areas containing thin line features while preventing the thin line growth from encroaching the non-thin line features.

18. The detection method of claim 17, wherein preventing the thin line growth from encroaching the plurality of geometries is accomplished by distinguishing the thin line and non-thin features.

19. The detection method of claim 17, further comprising a step of utilizing level-set function to measure critical dimensions for performing thin line detection.

20. The detection method of claim 17, wherein the step of restoring the mask pattern from the spot image allows more reliable segmentation and more accurate line width measurement.

21. The detection method of claim 17, wherein the spot image is a band limited low passed version of the mask pattern.

* * * * *